United States Patent [19]

Kopacz

[11] Patent Number: 4,632,906
[45] Date of Patent: Dec. 30, 1986

[54] BIODESULFURIZATION OF CARBONACEOUS MATERIALS

[75] Inventor: Elva P. Kopacz, Chicago, Ill.

[73] Assignee: Atlantic Richfield Company, Plano, Tex.

[21] Appl. No.: 676,346

[22] Filed: Nov. 29, 1984

[51] Int. Cl.$^4$ .................. C12R 1/07; C10G 32/00
[52] U.S. Cl. ............................. 435/282; 435/832
[58] Field of Search .......................... 435/282, 832

[56] References Cited

U.S. PATENT DOCUMENTS 2,521,761  9/1950  Strawinski ..................... 435/282
4,562,156  12/1985  Isbister et al. ................. 435/253

OTHER PUBLICATIONS

Chandra et al, "Fuel", 1980, vol. 59, pp. 249–252.
*Biotechnology & Bioengineering*, Wang (Ed.) vol. XXVI, (1984), John Wiley & Sons, Inc., N.Y., pp. 92–99.

Primary Examiner—Robert J. Warden
Assistant Examiner—Patricia Kate White
Attorney, Agent, or Firm—Wofford, Fails & Zobal

[57] ABSTRACT

A process for reducing the sulfur content of a sulfur-containing carbonaceous material by contacting it in an aqueous medium with the organism *Bacillus sulfasportare* per ATCC number 39909.

3 Claims, 1 Drawing Figure

Microphotograph I
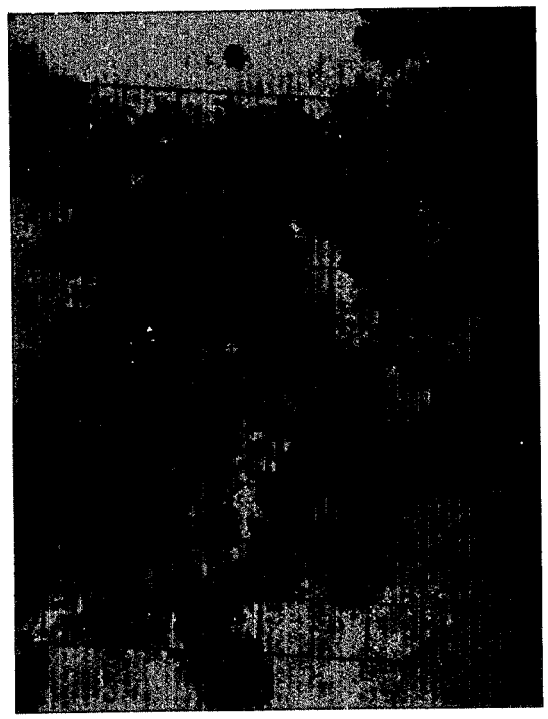

BIODESULFURIZATION OF CARBONACEOUS MATERIALS

BACKGROUND OF THE INVENTION

1. Field of the Invention

This invention relates generally to microorganisms, and processes employing microorganisms, having the ability to interact with organic sulfur found in carbonaceous materials.

2. Prior Art

The prior art teaches that bacteria which are found in acid coal mine drainage ditches are capable of removing inorganic sulfur (i.e., pyritic sulfur from coal by oxidation) producing sulfuric acid. For example, the article "Coal Desulfurization by Leaching Involving Acidophilic and Thermophilic Microorganisms", *Biotechnology & Bioengineering*, XXIV (1982), 743–748, discloses that the bacterial agent *Thiobacillus ferrooxidans* interacts with the inorganic pyritic sulfur associated with coal according to a reaction sequence which proceeds as follows:

$$FeS_2 + 3.5O_2 + H_2O \rightarrow FeSO_4 + H_2SO_4 \quad [1]$$

$$FeS_2 + 3O_2 + 2H_2O \rightarrow 2H_2SO_4 + Fe^{3+} \quad [2]$$

$$FeS_2 + Fe_2(SO_4)_3 \rightarrow 3FeSO_4 + 2S \quad [3]$$

The aforementioned reaction mechanism operates on inorganic sulfur only. Efforts to remove organic sulfur with this pyritic sulfur-removing bacteria have not been successful.

In an item in the publication *Fuel*, 58 (1979), 549–550, Chandra, et al., preliminarily reported microbial removal of organic sulfur from coal using *Thiobacillus ferrooxidans*. In a later publication, however, *Fuel*, 59 (1980), 249–252, Chandra, et al., report good inorganic sulfur removal and poor organic sulfur removal using a microorganism, presumably, *Thiobacillus ferrooxidans*. The article "Microbial Oxidation of Dibenzothiophene by the Thermophilic Organism *Sulfolobus Acidocaldarius*", *Biotechnology and Bioengineering*, XXVI (1984), 687–690, discusses *Sulfolobus acidocaldarius*, a thermophilic (60°–90° C.) reduced sulfur and iron oxidizing microorganism, that is a facultative autotroph. The microorganism was originally isolated from the acidic hot springs of Yellowstone National Park. Several high-temperature (70°–90° C.) strains of Sulfolobus have been isolated. The organism is acidophilic with a pH optimum of 2<pH<3 and is capable of using both reduced inorganic substrates (Fe$^2$ and reduced sulfur) and simple organic (carbohydrate) compounds as a source of energy. The organism has been used for sulfur (mainly pyritic sulfur) removal from coal and metal leaching from certain mineral sulfides.

This article reports an investigation of the oxidation of dibenzothiophene ($C_{12}H_8S$) using the thermophilic *Sulfolobus acidocaldarius* microorganism in a nutrient medium with dibenzothiophene as the sole source of carbon.

The article reports *Sulfolobus acidocaldarius* is capable of oxiding sulfur present in dibenzothiophene to sulfate. In addition, the article suggests that as a microorganism capable of oxidizing dibenzothiophene, *Sulfolobus acidocaldarius* may prove to be effective in removing thiophene compounds from waste water streams, coal and crude oil.

It is by no means obvious, however, that a microorganism which can oxidize pure dibenzothiophene would be effective in removing thiophene compounds from waste water streams, coal or crude oil. Actual effectiveness in these applications can only be shown by actual trials demonstrating such effectiveness.

Identification of microorganisms which can oxidize and/or aid in removal of organic sulfur from carbonaceous materials such as coal, petroleum coke and petroleum oils would be very desirable.

BRIEF DESCRIPTION OF THE DRAWINGS

FIG. 1 is a photomicrograph of 1200× magnification illustrating the microorganism of the invention.

SUMMARY OF THE INVENTION

A mutant strain of *Bacillus sulfasportare* having the ability to react with organic sulfur associated with carbonaceous materials has been invented. Further, the invention comprises the utilization of such a strain of *Bacillus sulfasportare* in a process for reducing the organic sulfur content of carbonaceous materials such as coal and petroleum oils.

DETAILED DESCRIPTION OF THE INVENTION

The particular strain of *Bacillus sulfasportare* utilized in the instant invention has been placed on deposit with the American Type Culture Collection and has been assigned identification No. ATCC 39909.

A microorganism culture was isolated from soil samples collected from an abandoned coal refuse site in Braidwood, Ill. Samples were collected from an area where coal and pyrite litter were scattered over moist soil. The area was devoid of higher plant life. Sampling depth did not exceed one inch. Soil samples were collected into sterile, covered glass jars.

The soil was determined to have a pH of 3. A soil sample was inoculated to the following aqueous mineral media:

| | |
|---|---|
| NH$_4$Cl | 0.050% |
| MgCl$_2$.6 H$_2$O | 0.025% |
| KH$_2$PO$_4$ | 0.025% |
| Dibenzothiophene | 0.10% |
| pH | 7.3 |

Metabolism of dibenzothiophene was selected for as follows. Sequential inoculations were made every 4–6 days. Cultures were incubated at 30° C. in shaker flasks. On the 22nd day of incubation, the bacteria were inoculated to mineral media to which beef extract (0.1%) had been added. The beef extract, by virtue of its nutrient properties, allowed for vast increases in the population of the selected organism. After 8 days of growth on the beef extract medium, a 10 ml. aliquot of bacteria was inoculated to a mineral medium where dibenzothiphene was the sole sulfur source. After 2 days of growth at 30° C., a large population of Gram positive cocci or rods was observed (Microphotograph I).

The sulfur-metabolizing isolate—the mutant organism of the invention—is referred to as *Bacillus sulfasportare*. The mutant organism is a Gram positive rod which removes organic sulfur from carbonaceous materials by an aerobic metabolic pathway. Bacterial growth occurs on a mixture of amino acids, but not on sugars. The organism is mesophilic and salt tolerant. The mutant reverts to the wild type when grown in the presence of yeast extract over a number of generations. The wild type is identical to the mutant described above, except endospres are formed when nutrients in the wild-type culture begin to diminish. The spores are ovoid and bipolar. Neither the wild-type bacterium nor the mutant strain conform to any category of Bacillus which is described in Bergey's Eighth Edition.

Bacillus sulfasportare* is a stable mutant of a member of the family Bacilliaceae. However, the soil sample from which *Bacillus sulfasportare* was obtained is a natural habitat for Thiobacillus. Thiobacillus derives energy from the oxidation of one or more reduced or partially reduced sulfur compounds, including sulfides, elemental sulfur, thiosulfate, polythionates, and sulfite. The final oxidation product is sulfate, but sulfur and polythionates accumulate transiently. The genus contains members whose oxygen requirements vary from strict to facultative aerobicism. Optimum temperature for growth ranges from 15°-30° C. and pH tolerances are wide. Morphologically, the genus is rod shaped. All members of the genus Thiobacillus strain are Gram negative. Resting spores are not formed.

When bacteria from the soil sample were selectively cultured for dibenzothiophene metabolism, there emerged an organism which was Gram positive and rod shaped (often growing in pairs of rods jointed end to end). After growth for 30 days on a yeast extract nutrient medium, *Bacillus sulfasportare* formed resting spores. This is seen as definitive evidence that the organism is not Thiobacillus. The spores formed are bipolar and oblong. They have not been observed in dibenzothiophene, thiosulfate, or vacuum resid media, but only in yeast extract cultures which are over 25 days old. When a culture which has sporulated is inoculated to fresh media, be it yeast extract or dibenzothiophene, the organism reverts to a growth phase and no resting spores are observed. When the culture is continued on yeast extract until exhaustion of the nutrient, sporulation occurs. When the culture remains on dibenzothiophene, however, sporulation does not occur.

*Bacillus sulfasportare*, in its wild form, "prefers" to utilize yeast extract. Following a period in which the organism has had only dibenzothiophene as a sulfur source and $CO_2$ as a carbon source, the organism becomes stably mutated to this metabolic pathway and also apparently loses its ability to form spores. When the stable mutant is transferred to yeast extract and allowed to grow on that medium for many generations, it reverts to the wild type. In its wild form, the organism produces spores if the yeast extract media begins to diminish.

The sulfur-metabolizing mutant of the invention, *Bacillus sulfasportare*, was inoculated to various sulfur-containing carbonaceous materials in a series of experimental runs.

*Bacillus sulfasportare* mediated the removal of sulfur from three carbonaceous matrices (namely, coal, vacuum residual oil, and atmospheric bottoms). Each matrix presents a different processing problem and, therefore, coal, vacuum residual oil and atmospheric bottoms are considered separately.

Referring first to the biotreatment of vacuum residual oil, sulfur removal ranged from 17-23 weight percent.

A description of the vacuum residual oil is presented below.

| VACUUM RESIDUAL OIL | | | |
|---|---|---|---|
| Sulfur | 4.21% | Gravity API | 3.96 |
| Carbon | 84.85% | KVis at 210° F. | 8778 CSt |
| Hydrogen | 9.88% | KVis at 275° F. | 708.5 CSt |
| Con. C | 26.78% | Nickel | 80 ppm |
| Ash | 0.10% | Vanadium | 430 ppm |
| Nitrogen | 0.63% | Iron | 11 ppm |
| | | Sp. Gr. | 1.0446 |

The vacuum residual oil is highly viscous at bioreactive temperatures. Even at a relatively high reaction temperature (38° C.), the oil is semi-solid and non-emulsible in the aqueous bacteria-containing media. Because bioreactions are dependent upon the amount of contact between bacteria and the vacuum residual oil matrix, steps were taken to increase the surface area of the oil with respect to water. Referring to Table 1, in a shaker flask, no sulfur removal was observed. When the surface area of the oil was increased through the use of a 2-liter stirred vessel in which oil was coated onto the walls of the vessel, 17 percent sulfur removal was obtained. An attempt to increase surface area by lowering the oil viscosity with a light petroleum oil cutter fraction so that an emulsion of oil in water was created brought to light another novel unexpected property of the bacterial action. The light petroleum oil cutter fraction, in this case heavy cycle oil, became stably emulsed in the aqueous matrix to the exclusion of resid. While the resid fraction sustained a sulfur reduction of 34 percent, the bacterium also mediated the emulsification of the light fraction.

When atmospheric bottoms from Maya crude were treated with *Bacillus sulfasportare*, 45 percent sulfur was removed. This improvement in sulfur removal from that observed for vacuum residual oil may be due to the lower degree of condensation of the lighter oil. The viscosity of the atmospheric bottoms was lower than that of vacuum residual oil, therefore allowing for improved bacteria-oil contact. Also, sulfur moieties may have been more readily available to attack.

The removal of organic sulfur from oil was very desirably not attended by coincident loss of carbon content. Therefore, in light of the oxygen dependence of the process, it is theorized that sulfur is removed by oxidation and cleaved from its hydrocarbon matrix without oxidation of carbon. This is opposed to the commonly observed pathway of oil degradation by bacteria which proceeds by sequential oxidation of the aromatic ring to catechol or protocatechuate followed by cleavage of the ring to 4-oxoadipate enol-lactone, and finally to succinate. That reaction sequence leads to desulfurization as the sulfur-holding species are broken. However, the loss of heating value through carbon oxidation is not desirable. While the pathway of sulfur removal in the process of the invention is not fully understood, it is hypothesized that the dibenzothiophene reaction proceeds by way of dibenzothiphene sulfone to dibenzofuran. Sulfur may be either eliminated by way of sulfate or may be incorporated into biomass as sulfur-containing amino acids. The ability of *Bacillus sulfasportare* to utilize $CO_2$ as its sole carbon source reinforces this hypothesis.

Sulfur removal from Pond Creek bituminous coal by *Bacillus sulfasportare* may have proceeded by a slightly different metabolic route than that which was followed during the treatment of resid. This coal has 1.39 percent total sulfur content, 0.71 percent of which is pyrite, the remainder being organic sulfur. There was no determination as to whether the pyrite or the organic sulfur or parts of both were removed.

Tables 1 and 2 below present specific details of sulfur removal from the three carbonaceous matrices discussed above. In all of the runs presented, the carbonaceous material was mixed with an equal quantity of the formulated mineral water described below under sterile conditions. The mixtures were inoculated with *Bacillus sulfasportare* and agitated in the manner, time and temperature set forth in Table 1. The aqueous portion of the mixture was then decanted from the carbonaceous material. The carbonaceous material was then washed with hot water, dried and analyzed for sulfur content and carbon and hydrogen content as indicated. The analytical results are presented in Table 2 below.

| FORMULATED MINERAL WATER | |
|---|---|
| $NC_4Cl$ | 0.050% |
| $MgCl_2.6\ H_2O$ | 0.025% |
| $KH_2PO_4$ | 0.025% |
| Distilled Water | Balance |
| pH | 7.3 |

TABLE 1

| RUN NO. | REACTOR VESSEL | MATERIAL | TIME DAYS | TEMP °C. | BAC. GROWTH | S REMOVAL % |
|---|---|---|---|---|---|---|
| 1 | Shake Flask | Pond Creek Coal | 30 | 30 | + | 24 |
| 2 | Shake Flask | Vac. Resid | 30 | 30 | + | 27 |
| 3 | Stirred Vessel | Vacuum Resid | 42 | 30 | + | 17 |
| 4 | Stirred Vessel | Vacuum/HCO Resid | 42 | 30 | + | 34 |
| 5 | Stirred Vessel | Atm. Bottoms | 37 | 38 | + | 45 |

In run No. 4, Heavy Cycle Oil (HCO) separated from resid and emulsed in water.

TABLE 2

| RUN NO. | SULFUR CONTENT UN-TREATED | SULFUR CONTENT TREAT-ED | C % UNTREATED | H % UNTREATED | C % TREATED | H % TREATED |
|---|---|---|---|---|---|---|
| 1 | 1.39% | 1.05% | — | — | — | — |
| 2 | 4.08% | 2.96% | — | — | — | — |
| 3 | 4.08% | 3.37% | 86.58 | 10.30 | 85.50 | 9.90 |
| 4 | 3.18% | 2.10% | — | — | — | — |
| 5 | 3.52% | 1.92% | — | — | — | — |

Unless otherwise stated, all parts ad percentages herein are on a weight basis.

As can be seen from Table 1 above, *Bacillus sulfasportare* removed substantial quantities of sulfur from the carbonaceous matrices. In addition, Table 2, which shows percent carbon (C) and percent hydrogen (H) of the carbonaceous matrix before and after treatment, shows that this sulfur removal can be desirably accomplished with an attendant loss of carbon.

The invention which is claimed is:

1. A method for reducing the sulfur content of a sulfur-containing carbonaceous material comprising contacting a sulfur-containing carbonaceous material in an aqueous medium with a microorganism *Bacillus sulfasportare* per American Type Culture Collection number 39909.

2. The method of claim 1 wherein said carbonaceous material is coal.

3. The method of claim 1 wherein said carbonaceous material is a hydrocarbon oil.

* * * * *